US006261589B1

(12) United States Patent
Pearson et al.

(10) Patent No.: US 6,261,589 B1
(45) Date of Patent: Jul. 17, 2001

(54) DIETARY SUPPLEMENT NUTRIENT SOFT DRINK COMPOSITION WITH PSYCHOACTIVE EFFECT

(76) Inventors: Durk Pearson; Sandy Shaw, both of P.O. Box 2160, Tonapah, NV (US) 89049

( * ) Notice: Subject to any disclaimer, the term of this patent is extended or adjusted under 35 U.S.C. 154(b) by 0 days.

(21) Appl. No.: 09/518,223

(22) Filed: Mar. 2, 2000

Related U.S. Application Data

(60) Provisional application No. 60/122,329, filed on Mar. 2, 1999.
(51) Int. Cl.[7] .................................................. A61K 47/00
(52) U.S. Cl. ............................................. 424/439; 424/400
(58) Field of Search ..................................... 424/439, 400

(56) References Cited

U.S. PATENT DOCUMENTS

| | | | |
|---|---|---|---|
| 5,403,826 | * 4/1995 | Cope et al. | 514/21 |
| 5,480,872 | * 1/1996 | Cope et al. | 514/21 |
| 5,571,441 | * 11/1996 | Andon et al. | 252/1 |

* cited by examiner

Primary Examiner—Thurman K. Page
Assistant Examiner—Robert M. Joynes
(74) Attorney, Agent, or Firm—Law Offices of Royal W. Craig

(57) ABSTRACT

A composition and method for causing a positive psychoactive effect in which phenylalanine, vitamin B-6, vitamin C, copper, folic acid, taurine, vitamin B-5 (or pro-vitamin B-5), choline, fruit sugar, caffeine, and optionally green tea are combined in a carbonated mixture. The mixture is orally administered in beverage form to support the production of and to stimulate release of neurotransmitters and neuromodulators in the brain and to enhance and modulate their effects to produce a positive psychoactive effect.

3 Claims, No Drawings

DIETARY SUPPLEMENT NUTRIENT SOFT DRINK COMPOSITION WITH PSYCHOACTIVE EFFECT

CROSS-REFERENCE TO RELATED APPLICATIONS

The present application is based upon and gains priority from U.S. Provisional Patent Application Serial No.: 60/122,329, filed: Mar. 2, 1999 by the inventors herein and entitled "DIETARY SUPPLEMENT NUTRIENT SOFT DRINK COMPOSITION WITH PSYCHOACTIVE EFFECT".

BACKGROUND OF THE INVENTION

1. Field of the Invention

The present invention relates to soft drinks and, more particularly, to an improved dietary supplement nutrient soft drink composition and method for taking the same to induce an uplifting psychoactive effect by promoting bodily production of noradrenaline, dopamine, acetylcholine and beta phenylethylamine.

2. Description of the Background

The most common complaint that doctors hear is that their patients don't have enough energy or feel tired most of the time. The cause is often a nutritional deficiency. A nutritional survey by the U.S. Department of Agriculture of 37,000 Americans (chosen to represent a cross-section of all Americans) found that over 80% of Americans are getting less than the FDA's recommended RDA for one or more nutrients that are essential for the production of noradrenaline and dopamine. A shortage of these essential nutrient enzyme co-factors results in chronic tiredness. It would be helpful to provide a nutritious, non-prescription, inexpensive and flavorful solution that can be administered in the form of a soft drink.

There have been prior clinical attempts to find a solution. For example, U.S. Pat. No. 4,624,852 issued to Wurtman shows a process and composition for treating neurological disorders and aging by potentiating the effect of neurotransmitters in the brain. The process entails the concomitant administration of choline or a choline precursor, and an amino acid (which is a precursor to a neurotransmitter) such as tyrosine, tryptophan or threonine. This combination results in increased release of both their corresponding neurotransmitters, i.e., (a) acetylcholene and (b) dopamine, serotonin or glycine. The choline or choline precursor and amino acid are administered concomitantly to treat neurological disease including senility, Alzheimer's Disease or Parkinson's Disease. It is also said to be useful in normal older people, or younger people with obscure deficits in neurons releasing particular neurotransmitters.

While the above-described treatment may be helpful, it is narrowly directed to increasing bodily production of acetylcholene and dopamine by clinical concomitant administration of choline and an amino acid such as tyrosine or threonine. There are also a number of similar consumer-directed organic products to treat various problems. For example, InterNutria, Inc., manufactures a product known as PMS Escape. This is a dietary supplement to help manage normal disturbances in mood and appetite associated with premenstrual syndrome. PMS Escape is a blend of simple and complex carbohydrates, in the form of dextrose, maltodextrin and potato starch, as well as calcium, vitamin C, magnesium and vitamin B-6. All ingredients are recognized food ingredients, vitamins or minerals that work naturally to boost the normal level of serotonin (a neurotransmitter which regulates mood, appetite and memory). The product is sold in the form of a powdered drink mix.

Similarly, it would be greatly advantageous to provide an organic composition and method for increasing energy and awareness via an integrated system of nutrients to deliver scientifically designed dietary supplements to the brain.

SUMMARY OF THE INVENTION

It is, therefore, an object of the present invention to provide a natural organic composition of nutrients and method for administration of the same to increase energy and for generally increasing awareness in both males and females.

It is another object to provide the above-described benefits via an organic, non-prescription, inexpensive and flavorful solution that can be administered in the form of a soft drink.

According to the present invention, the above-described and other objects are accomplished by providing a composition and method for causing a positive psychoactive effect in which phenylalanine, vitamin B-6, vitamin C, folic acid, copper, taurine, choline, vitamin B-5 or provitamin B-5, fruit sugar, optionally the addition of non-caloric natural or artificial sweetener like astevia or aspartame, caffeine, and (optionally) green tea are combined in a carbonated mixture. The mixture is orally administered in beverage form to facilitate the production of and to stimulate release of neurotransmitters and neuromodulators in the brain to produce a positive psychoactive effect.

DETAILED DESCRIPTION OF THE PREFERRED EMBODIMENTS

Every thought, every memory and every emotion, even the will to move a muscle is caused by the release of neurotransmitters in your brain. Neurotransmitters are natural, substances made from nutrients by neurons in the brain.

The most thoroughly researched neurotransmitters are noradrenaline, dopamine, and acetylcholine, and each is involved in many different processes.

Noradrenaline plays an important role in brain processes for fast memory, quick reaction time, mental energy, alertness and attention, goal seeking, and sexual behavior.

Dopamine is part of the reward and pleasure circuitry, sex, coordinated motor activity, and also important in what is called, "effortful" memory (where you have to "search" around for what you are trying to remember).

Acetyloholine is central to focus, concentration, memory, and verbal behavior.

The present inventors have found an organic means for providing the brain with nutrient raw materials they need to increase their supplies of the neurotransmitters noradrenaline (also called norepinephrine, the brain's version of adrenaline), dopamine, and acetylcholine, as well as the neuromodulators taurine and beta phenylethylamine. This effectively increases energy levels and general awareness. Thus, the present invention is a combination of organic nutrients aimed at stimulating the brain to produce a positive psychoactive effect, coupled with a delivery medium to effectively deliver the nutrient combination to the brain, and a regimen for administering the combination to effectively maintain a personal mental fitness program.

The basic active constituents include phenylalanine, folic acid, copper, vitamin C, vitamin B-6, taurine, choline, vitamin B-5 (or provitamin B-5), fructose and carbon dioxide. These constituents are incorporated in a carrier solution as follows (all constituents and acceptable dosages):

| Dose (mg or i.u.) | Constituent |
|---|---|
| 160 | Provitamin B-5 (as pantothenyl alcohol) |
| 500 | Phenylalanine |
| 400 | Taurine |
| 112.5 | Vitamin C (niacinamide ascorbate) |
| 50 | Vitamin C (ascorbic acid) |
| 50 iu | Vitamin E |
| 300 | Choline (as di-hydrogen citrate) |
| 150 | Glycine |
| 10 | Vitamin B-6 |
| 200 | Malic Acid |
| 3 | Vitamin B-2 |
| 3 | Zinc (as Zinc gluconate) |
| 0.42 | Copper (as copper gluconate) |
| 1.5 | Vitamin B-1 (thiamine) |
| 0.05 | Chromium (as chromium chloride) |
| 5.1 | Aspartic Acid |
| 3 vol | Carbon Dioxide |
| 8.4 oz | Water |
| 0.15 | Folic Acid |

The primary active constituents have the following advantages:

Phenylalanine

The essential nutrient amino acid L-phenylalanine contained in the formulation can be converted by the brain into neurotransmitters noradrenaline and dopamine with the help of the essential nutrient enzyme cofactors folic acid, vitamin C, copper, and vitamin B-6 and into the neuromodulator beta phenylethylamine with the help of the essential nutrient enzyme co-factors copper and vitamin B-6.

Vitamin B-6, Copper, Vitamin C and Folic Acid

Phenylalanine can also be used by the brain to make a natural neuromodulator beta-phenyethylamine (modulates, the effects of neurotransmitters). Phenylalanine is converted into beta-phenylethylamine by the enzyme aromatic amino acid decarboxylase. This enzyme is dependent on both vitamin B-6 (about 80% of the population receives less than the RDA) and copper (about 40% of the population receives less than the RDA). This enzyme and its B-6 and copper cofactors is also required to convert phenylalanine into noradrenaline and dopamine, which also requires vitamin C and folic acid. Beta-phenylethylamine modulates the effects of noradrenaline and dopamine. It has been found that beta-phenylethylamine seems to intensify emotional experiences and may even provide a subtle euphoria. It is interesting to note that chocolate is the best food source of pre-formed beta-phenylethylamine.

Taurine:

The present invention includes another neuromodulator, the natural nutrient sulfur-containing amino acid taurine, which is important in the regulation of electrically active tissues (such as the heart and brain), to modulate the activating effects of noradrenaline. Taurine helps prevent excessive sensitivity to noradrenaline, which may be experienced subjectively as jitteriness and overstimulation. Taurine helps to promote a mellow mood without sedation or tranquilization. The best food source of taurine is red meat.

Vitamin B-5 (or Pro-vitamin B-5) and Choline

Acetylcholine is made in the brain from choline with the help of vitamin B-5. The present invention includes substantial amounts of both choline and B-5, preferably in the form of pro-vitamin B-5 (pantothenol alcohol) which is more stable in aqueous solution than pantothenic acid and its salts. The increased levels of B-5 can be used to increase levels of acetylcoenzyme A, from which the enzyme choline acetyltransferase transfers an acetyl group to choline to form acetylcholine. It is interesting to note that fish has been traditionally referred to as brain food, and is fish is a good food source of choline.

Fruit Sugar (Fructose):

Fruit sugar: The present invention is naturally sweetened with pure fruit sugar, and includes natural fruit flavors. However, the fruit sugar does more than provide a sweet flavor. It also helps inhibit hepatic gluconeogenesis. When a person does not eat for hours, their blood sugar may fall low enough for gluconeogenesis to be switched on in the liver. When this happens, the liver converts amino acids (such as phenylalanine) circulating in the blood into glucose, the major cellular fuel, in order to get blood glucose levels back up. If this happens, less of the essential nutrient amino acid phenylalanine may get into the brain. Fruit sugar helps to prevent this loss of phenylalanine (through gluconeogenosis) without releasing significant amounts of insulin. This is not done by glucose (grape sugar) or sucrose (cane or beet sugar), and their release of insulin can do two things: 1) it can promote the uptake of phanylalanine by other tissues in the body leaving less for the brain, and 2) it can eventually lower the blood sugar even further (by causing glucose to leave the bloodstream), thereby causing an unwelcome blood sugar roller coaster ride, and further destruction of circulating blood free amino acids by gluconeogenisis.

Fruit sugar has another advantage over glucose, sucrose, or the common "high" fructose corn syrup (which contains only about 55% fructose); it in 70% sweeter than ordinary sugar under the cold acid conditions occurring when the present beverage is chilled. This favors more sweetness from fewer calories than ordinary soft-drinks. Indeed, the present composition has only 82 calories per serving, about 60% that of a typical soft drink.

Caffeine

Like most cola drinks, the present invention contains 40 mg. of caffeine per serving. An average cup of instant coffee contains about 60–80 mg. of caffeine. A typical cup of fresh brewed coffee contains about 110–130 mg. caffeine, with espresso having 250–500 mg. Scientific studies have shown that the right dose of caffeine can improve speed and accuracy in a wide variety of practical tasks, such as typing. Everyone who uses caffeine knows that the first cup of coffee in the morning is the best and helps gets you going. But the second cup doesn't do as much, and the third cup gives you even less. By the end of a long hard day, coffee doesn't seem to help at all and can cause irritability. To understand why this happens it helps to understand how caffeine works. One of the ways that caffeine works is to cause neurons to release noradrenaline more readily and to be more sensitive to the effects of noradrenaline. However, caffeine or coffee, tea, or ordinary soft drinks do not provide the nutrients required to make more noradrenaline, so it is like burning your candle at both ends. Caffeine can give one extra energy and even better performance on certain types of tasks, but it can also cause a letdown when it makes you use the noradrenaline faster than the body can make more. The amount of caffeine in the present invention along with the other nutrients that help to make noradrenaline will give long-lasting mental energy.

Green Tea:

The present composition optionally employs green tea extract which supplies 140 mg. of green tea polyphenols per serving (about as much as is found in a cup of green tea).

Green tea polyphenols are very powerful natural phytochemical antioxidants and free radical scavengers. They also chelate transition metal free radical catalysts such as iron. There are literally hundreds of published scientific studies an the effects and potential health benefits of green tea and green tea polyphenols. These studies range from mechanistic chemistry experiments to tissue cultures to animal experiments to epidemiological studies in humans. Green tea polyphenols have substantial (but not perfect) cancer prevention effects in many tissue cultures and animal experiments. Studies comparing human populations who either do (or do not) drink about five cups or more of green tea per day suggest that green tea may reduce the risk of some types of cancers, particularly those of epithelial tissues, such as the skin and the tissues lining the gut and lungs. Most common human cancers are found in these tissues. The green tea polyphenols of the present invention also contribute to the psychoactive effect. The brain is the most fatty organ in the body, it is the most polyunsaturated, it has a high specific metabolic rate so it produces many free radicals, and it has the least capability to repair damage. Free radicals love to attack fat, and are especially avid at attacking the highly polyunsaturated fat found in the brain. It is believed that when green tea free radical scavenging antioxidant polyphenols enter the brain, a feeling of well-being results and this is the brain's way of positive reinforcement.

Carbonated Carrier

Carbon Dioxide bubbles go straight to the brain. For instance, when one drinks champagne the effects of the alcohol come on faster and stronger than with an equal amount of still wine containing the same amount of alcohol. This is because carbon dioxide released in the mouth immediately travels to tissues in the nasal passages, dissolves in the blood there, and is transported directly to the blood-brain barrier, the selective membrane that surrounds the brain. This has two effects: 1) the carbon dioxide causes vasodilation (increasing blood flow to and within the brain), and 2) the $CO_2$ also increases the permeability of the blood-brain barrier, letting in more alcohol (or the nutrients of the present composition) faster. Thus, the carbonation of the present invention acts as a transport and penetration aid which makes the onset of the psychoactive effect more rapid and intense.

Administration Regimen

For best results, it has been found that one serving of the present invention should be taken between meals, at least an hour before the meal. This is because proteins from food are broken down into amino acids, some of which can compete for transport, thereby reducing the rate of phenylalanine uptake from the gut or transport across the blood-brain barrier into the brain.

Of course, in addition to the above-described active ingredients, further inert ingredients may be added as desired to achieve a desired taste, color or consistency.

Having now fully set forth the preferred embodiment and certain modifications of the concept underlying the present invention, various other embodiments as well as certain variations and modifications of the embodiments herein shown and described will obviously occur to those skilled in the art upon becoming familiar with said underlying concept. It is to be understood, therefore, that the invention may be practiced otherwise than as specifically set forth herein.

What is claimed is:

1. A composition for causing a positive psychoactive effect, comprising:

phenylalanine in the amount of approximately 200–1500 mg;

vitamin B-6 in the amount of approximately 1–20 mg;

vitamin C in the amount of approximately 30–1000 mg;

copper in the amount of approximately 0.1–1 mg;

folic acid in the amount of approximately 0.05–0.4 mg;

choline in the amount of approximately 100–1000 mg;

taurine in the amount of approximately 100–1500 mg;

one from among the group comprising provitamin B-5 and vitamin B-5 in the amount of approximately 10–500 mg;

fruit sugar in the amount of approximately 7–30 g;

caffeine in the amount of approximately 20–200 mg;

carbonated dioxide in the amount of approximately 1–5 volumes;

water;

said constituents being orally administered in beverage form to stimulate release of neurotransmitters in the brain and to enhance and modulate their effect via formation and release of the neuromodulator beta phenylethylamine, by supplying the neuromodulator taurine, and by supplying caffeine to produce a positive psychoactive effect.

2. The composition for causing a positive psychoactive effect according to claim 1, further comprising green tea polyphenols in an amount of approximately 10–400 mg.

3. A method for causing a positive psychoactive effect using the composition of claim 1, comprising the steps of:

combining said phenylalanine, vitamin B_6, vitamin C, copper, folic acid, choline, taurine, pro-vitamin B_5, fruit sugar, caffeine, and carbonated dioxide, with water in a carbonated mixture;

orally administering said mixture to support the production of and to stimulate release of neurotransmitters and neuromodulators in the brain and to enhance and modulate their effects to produce a positive psychoactive effect.

* * * * *